(12) United States Patent
Kim

(10) Patent No.: US 7,720,615 B2
(45) Date of Patent: May 18, 2010

(54) SYSTEM FOR DETECTION AND PREDICTION OF WATER QUALITY EVENTS

(75) Inventor: Peter S. Kim, Minoa, NY (US)

(73) Assignee: Sensis Corporation, East Syracuse, NY (US)

( * ) Notice: Subject to any disclaimer, the term of this patent is extended or adjusted under 35 U.S.C. 154(b) by 107 days.

(21) Appl. No.: 11/684,048

(22) Filed: Mar. 9, 2007

(65) Prior Publication Data

US 2007/0233397 A1  Oct. 4, 2007

Related U.S. Application Data

(60) Provisional application No. 60/783,923, filed on Mar. 20, 2006.

(51) Int. Cl.
 *G06F 19/00* (2006.01)
 *C12Q 1/02* (2006.01)
(52) U.S. Cl. .................. 702/25; 702/1; 435/29
(58) Field of Classification Search ............ 702/25, 702/1; 435/29
 See application file for complete search history.

(56) References Cited

U.S. PATENT DOCUMENTS

| | | | | |
|---|---|---|---|---|
| 5,294,315 | A * | 3/1994 | Cooper et al. | 204/158.2 |
| 6,303,027 | B1 * | 10/2001 | Nagaiwa et al. | 210/143 |
| 6,536,272 | B1 * | 3/2003 | Houston et al. | 73/170.29 |
| 6,845,336 | B2 * | 1/2005 | Kodukula et al. | 702/118 |
| 2004/0130714 | A1 * | 7/2004 | Gellerman et al. | 356/300 |
| 2005/0164333 | A1 * | 7/2005 | Vincent | 435/34 |
| 2005/0267376 | A1 * | 12/2005 | Marossero et al. | 600/511 |
| 2006/0034731 | A1 * | 2/2006 | Lewis et al. | 422/88 |

OTHER PUBLICATIONS

Throckmorton, Jeff, "Breakthroughs in Real-time Monitoring of Water Quality in the Distribution System", Homeland Security Technologies, Hach HST Proprietary, Sep. 2005 from Hach's Product web seminars, pp. 1-36.
Hach, Hach Event Monitor Trigger System, Jul. 15, 2009, as available from http://www.hach.com, 1 page.

* cited by examiner

*Primary Examiner*—Eliseo Ramos Feliciano
*Assistant Examiner*—Janet L Suglo
(74) *Attorney, Agent, or Firm*—Burr & Brown

(57) ABSTRACT

A method of evaluating a water sample for the presence or possible future presence of nitrification comprises obtaining data values of a number of parameters, processing the data values to determine correlation coefficients, to identify any linear dependencies, to standardize the scales, evaluating the data values over a plurality of proliferation time periods and neuron numbers, calculating MSEs and $R^2$'s from the evaluations, and estimating a valid likelihood of nitrification of the water sample. A method of evaluating a water sample for the presence or possible future presence of nitrification, comprises obtaining data values of a number of parameters, statistically pre-processing the data values and supplying the pre-processed data values to a neural network. Apparatus, media and processors which are used in performing such methods.

25 Claims, 16 Drawing Sheets

| pH | TEMP. | COND. | TOTAL CHLORINE | TURB. | DO | TOC | NH3 | NITRITE |
|---|---|---|---|---|---|---|---|---|
| 1.00 | -0.03 | 0.07 | 0.10 | -0.05 | -0.03 | -0.15 | 0.03 | 0.06 |
| -0.03 | 1.00 | 0.42 | 0.08 | -0.07 | -0.03 | -0.31 | -0.12 | 0.42 |
| 0.07 | 0.42 | 1.00 | 0.37 | -0.19 | 0.28 | -0.40 | -0.13 | -0.10 |
| 0.10 | 0.08 | 0.37 | 1.00 | -0.34 | 0.21 | -0.23 | -0.02 | -0.29 |
| -0.05 | -0.07 | -0.19 | -0.34 | 1.00 | -0.26 | 0.10 | 0.02 | 0.09 |
| -0.03 | -0.03 | 0.28 | 0.21 | -0.26 | 1.00 | 0.28 | 0.03 | 0.05 |
| -0.15 | -0.31 | -0.40 | -0.23 | 0.10 | 0.28 | 1.00 | 0.07 | 0.23 |
| 0.03 | -0.12 | -0.13 | -0.02 | 0.02 | 0.03 | 0.07 | 1.00 | -0.15 |
| 0.06 | 0.42 | -0.10 | -0.29 | 0.09 | 0.05 | 0.23 | -0.15 | 1.00 |

*FIG. 4*

SYSTEM FOR DETECTION AND PREDICTION OF WATER QUALITY EVENTS

CROSS-REFERENCE TO RELATED APPLICATION

This application claims the benefit of U.S. Provisional Patent Application No. 60/783,923, filed Mar. 20, 2006, the entirety of which is incorporated herein by reference.

FIELD OF THE INVENTION

This invention relates to the industry of water quality control and more specifically to an apparatus and method for detecting and predicting general water quality events in water supplies. This invention, as an apparatus and method for predicting these water quality events, will allow for preventative measures to be taken before such water quality events threaten the safety of the water supply.

BACKGROUND OF THE INVENTION

Preventative management of water supplies is not only useful in keeping society safe and prosperous but also critical in avoiding the cost of potentially expensive reactive measures that may be necessary to resolve contamination. There is a wide variety of potential sources for contamination of such water supplies, including naturally-occurring phenomena as well as human-induced events. History demonstrates the pervasiveness of such threats and the future beckons for an accurate and reliable apparatus and method for detecting and predicting whether such water supplies are and will be contaminated.

Water quality events which may contaminate the water supply include a variety of chemical and biological processes and agents. Examples of such water quality events include nitrification, algae bloom, and deliberately sabotaging a water supply with bacteria like *Escherichia coli*. The example of nitrification is one that demonstrates how the detection and prediction of such an event can avert a potentially threatening and costly situation. Nitrification is a microbial process by which reduced nitrogen compounds, primarily ammonia, are sequentially oxidized to nitrite and nitrate by ammonia oxidizing bacteria and nitrite oxidizing bacteria, respectively. Nitrification must be avoided or controlled because of its potential effect on disinfectant residuals, which must be maintained at regulatory levels to ensure water safety. Nitrification can become a pervasive, persistent problem if allowed to develop, creating chronic disinfection residual challenges and the potential for unsafe water in the distribution system. The appearance of nitrate, via the formation of nitrite, in addition to the decrease of ammonia and total chlorine in the water, are the commonly known indicators that nitrification is occurring. In fact, there may be a number of other indicators among measurable water quality parameters that may signify the presence or impending onset of nitrification.

The fact that the relationships of these water quality parameters to particular water quality events are not readily understood or defined, coupled with the reality that the data for such parameters are often dynamic, noisy, and non-linear in fashion, contributes to the lack of a proactive system to accurately and reliably forecast water quality conditions. Instead, current monitoring systems employ passive methods to observe and manage water supplies. There exists a need for a flexible system with the capability to provide on-line, real-time evaluation of these water quality parameters in order to not only detect but also predict potentially harmful water quality events. The expression "real-time", as used herein, refers to simultaneous as well as slightly delayed (i.e., substantially real-time or delayed by a relatively short period of time, e.g., not more than one second, not more than one minute, not more than one hour, or not more than one day). With such a system, water quality control officials will have more options with which to deal with threatening water quality events and will be able to utilize preventative and proactive management strategies to minimize the costly impact of such threats.

BRIEF SUMMARY OF THE INVENTION

This invention provides an apparatus and method for detecting the likelihood that a particular water condition exists and/or predicting the likelihood that a particular water condition will exist at one or more specific times in the future and/or predicting the level at which a particular water quality condition will exist at one or more specific times in the future. The apparatus and method of this invention can, if desired, be capable of making such detections and predictions for any number of water quality conditions.

Water quality is affected by and this invention utilizes a number of physical, chemical, and biological water quality parameters. Physical water quality parameters are those of or relating to the material properties of water, and those which are measurable include pH, temperature, turbidity, and conductivity. Chemical water quality parameters are those of or relating to the chemical properties of water or the chemical compounds that may be found in water, and those which are measurable include ammonia, nitrite, nitrate, free chlorine, total chlorine, dissolved oxygen, total organic carbon, chlorophyll, and phycocyanin. Biological water quality parameters are those of or relating to biological organisms that may be found in water and may include the level of *Escherichia coli*, for instance.

Data for these water quality parameters are procured either by user or real-time sensors, although most probably by real-time sensors, from a water sample. The expression water sample as used herein refers to one of a plurality of successive water samples taken from or remaining within a body of water, e.g. a river, a lake, an ocean, a reservoir, a water treatment facility, a canal, a swimming pool, an aquarium, a reflecting pool, etc., and/or to a specific volume of water, e.g. contained within a beaker, which may have been obtained from any possible source. In some cases, the condition(s) for which the apparatus or method of the invention is testing, i.e., estimating the likelihood that the condition exists or will exist, is among the conditions (if any) being sensed or determined, in which case the apparatus or method can serve either to tend to confirm the result or to raise doubt as to the result of such sensing or determining.

The water quality data that is procured must be location specific and in time series. Location specific data is data in which all values in the data series are collected at the same location, and time series data is data in which all successive values in the data series represent consecutive measurements taken at equally spaced time intervals. This is important to identify the nature of the phenomenon represented by the sequence of observations pertaining to the specified environment and to be able to extrapolate the identified pattern to predict future values and trends.

After the historical water quality data is procured, it is evaluated by a water quality control inference engine (WQCIE), described in more detail below, which is comprised of neural network applications which preprocess the data, determine certain properties of the network architecture, and which trains, tests, and applies the network. The data is statistically preprocessed using any of a number of data analysis techniques. These data analysis techniques may include trend analysis, correlation coefficient analysis, linear regression, and data normalization Then two critical model properties, the optimal number of neurons and optimal time delay period, are determined (and/or selected). In some embodiments, the data is also separated into three data sets, a training set, a cross validation set, and a test set. Using these model properties and the training and cross validation sets, the neural network is trained. The third set of data is used to test the network.

After modeling of the network is complete, the system is ready to evaluate real-time water quality data, gathered in the same manner specified above.

BRIEF DESCRIPTION OF THE FIGURES

A full understanding of the invention can be gained from the following detailed description of the invention when read in conjunction with the accompanying figures in which:

FIG. 4 is a table showing the correlation coefficients calculated between various water quality parameters in an example of nitrification prediction.

Figure 1:
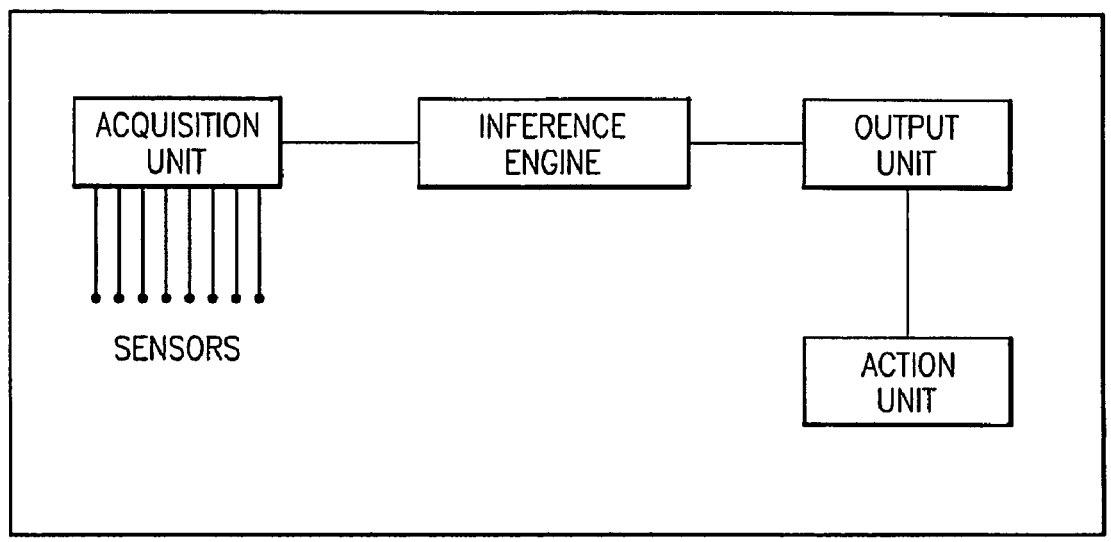
FIG. 1 is a block diagram of a preferred embodiment of an apparatus for the detection and prediction of water quality events.

In the Figures, conventional flow chart legends are used, i.e., a process is depicted as a rectangle, a decision is depicted as a diamond-shape, a manual operation is depicted as a trapezoid, data is depicted as a rhombus, a display is depicted as an oval-like shape and a document is depicted as a rectangle with a wavy bottom side.

DETAILED DESCRIPTION OF THE INVENTION

As noted above, the apparatus according to the present invention employs a neural network which receives real-time data for a number of water quality parameters, and which predicts future values for one or more of the water quality parameters. For instance, in a representative example of an apparatus according to the present invention, the apparatus is used to predict values for a "target parameter", namely, nitrite levels (i.e., in order to predict an onset of nitrification), based on collected location-specific data for a selected set of other parameters ("input parameters") as well as collected data for nitrite level ("target parameter"). In this representative example, the input parameters include pH, turbidity, conductivity, temperature, dissolved oxygen (DO), total organic carbon, ammonia and total chlorine. The collected data for each of the parameters (i.e., the eight input parameters and the target parameter) is collected with a specific frequency (e.g., every hour on the hour).

There are a number of well-known algorithms (referred to herein as "optimization algorithms") which are capable of recognizing patterns or trends in data, and fitting known patterns or trends to emerging data so as to anticipate future trends that the data will exhibit if it follows the known pattern or trend. In addition, as is likewise well-known, such optimization algorithms are capable of performing such curve-fitting or pattern-recognizing functions where input parameters are related to a target parameter in a non-linear fashion. One example of an optimization algorithm which is suitable for use in the present invention is a Levenberg-Marquardt network model.

In a representative example of an apparatus and method according to the present invention, the data for each parameter is statistically pre-processed using one or more data analysis techniques, e.g., any of the data analysis techniques identified above (namely, trend analysis, correlation coefficient analysis, linear regression and data normalization).

Next, in this representative example, using the pre-processed data, in the manner described below, a selection is made as to a combination of the number of neurons to be employed in the neural network and the time delay period (i.e., the length of time between the current time and the time in the future for which the nitrite value is predicted) to be employed. In doing so, (1) there is input a range of possible values for the number of neurons (e.g., from 2 to 15 neurons) from which the number of neurons to be employed will be selected, (2) a time delay application is employed to create a number of different possible time delay periods from which the time delay period to be employed will be selected (alternatively, a group of possible time delay values can be input), and (3) a location-specific time series collection of data is input. The optimization algorithm analyzes the data and, by analyzing how closely it can curve-fit the data, facilitates selection of an optimal combination of neuron number and time delay by, for each possible combination of neuron number and time delay (i.e., combinations of neuron number within the range of choices and time delay within the range of choices), determining optimal weights and bias factors so as to minimize the discrepancy between nitrite levels projected by the curve-fitting and the actual nitrite levels. By "weights" is meant, for each neuron in the neural network, the weights given to respective input parameters in predicting the value of the target parameter at a future time, i.e., a time which is spaced from the present time by the time delay; by "bias factor" is meant the relative weights given to each of the neurons. In other words, for each combination of (1) a neuron number within the range of possible neuron number values and (2) time delay within the possible time delay values, the optimization algorithm (in this representative example, a Levenberg-Marquardt algorithm) determines optimum weights and bias factors in order to best curve-fit the input collection data. The apparatus then evaluates how accurately the nitrite values in the input collection data would have been predicted (i.e., using data up to a particular time to predict nitrite value at a time which is in the future by an amount of time equal to the time delay) using those curve fitting weights and bias factors.

In this representative example, error values are generated for each combination of neuron number and time delay, whereby a combination of neuron number to be employed in the neural network and time delay to be employed can readily be selected. In general, a lower number of neurons is desirable, and so one particular combination of neuron number and time delay might be selected in favor of another combination of neuron number and time delay which has a lower error value, e.g., where the neuron number in the first combination is lower than the neuron number in the second combination.

Alternatively, a specific number of neurons to be employed can be input and the time delay period can be optimized, or a specific time delay period to be employed can be input and the number of neurons can be optimized.

Next, based on the selection of a specific number of neurons to be employed and a specific time delay, the apparatus in this representative example is optionally trained using a larger set of time-series location specific data (which may or may not include the data used in selecting the number of neurons and the time delay) in order to further optimize the curve-fitting accuracy for the prediction of nitrite values. In performing such training, any desired initial values can be input for the weights and bias factors, e.g., the weights and bias factors generated in the step of determining the number of neurons and time delay to be employed. Regardless of the initial values for the weights and bias factors, using a given body of data, the optimization algorithm will ultimately arrive at the same optimal values (typically, the closer the initial values are to the final values, the lower the processing time required).

Next, the apparatus in this representative example can optionally be tested for accuracy using a different collection of time-series location specific data, in order to provide additional evaluation as to how accurately the apparatus can predict nitrite levels.

Similar representative examples of suitable apparatuses can be provided in an analogous manner for any other target parameter using any other groups of input parameters.

During the application of the apparatus according to the present invention to real-time data, such real-time data is fed to the neural network, and the neural network outputs predicted future values for the nitrite level (i.e., the predicted value is the value which is expected to occur a period of time, equal to the time delay, after the present time), The devices according to the present invention can further employ a transfer function to the values output by the neural network. Any suitable transfer function can be employed, a variety of which are well-known by and readily available to persons skilled in the art, e.g., a hard limit transfer function, a sigmoidal transfer function or a linear transfer function (or even a transfer function which has little or no effect on the output), such transfer functions being well-known to those skilled in the art.

If desired, the device can be re-trained at any time or at regular intervals, e.g., every three months.

FIG. 1 is a block diagram of a preferred embodiment of an apparatus according to the present invention. The device may include an acquisition unit that may include sensors to obtain water quality data from a water sample, not shown, an inference engine, an output unit, and an action unit. The acquisition unit may receive water quality data from a recorded data source for analysis, but preferably receives real-time, on-line data through the sensors that are monitoring the water sample. The inference engine is comprised of all of the neural network applications that will generate and apply the neural network, in addition to preparing and validating the data. The output unit may include a screen to display the target parameter and predicted data or may alternatively or additionally feed an output signal to an action unit for possibly sounding an alarm or delivering the appropriate preventative means to avoid an impending water quality event.

Figure 2A:
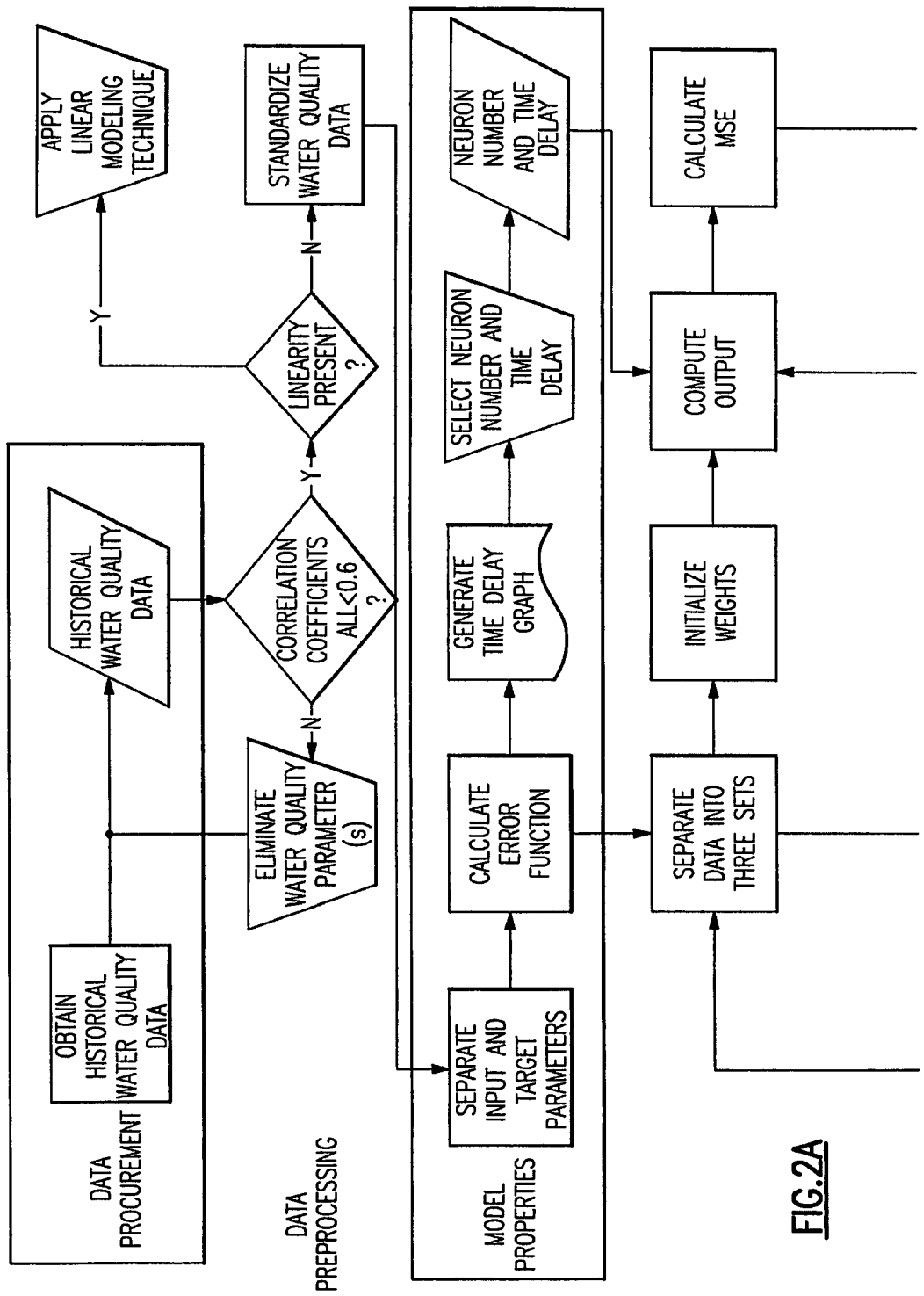
FIGS. 2a and 2b is a flow chart showing Phase I of neural network modeling, that is, the generation of the model. More specifically, it shows how the procured data is preprocessed, how the neural network is modeled, how the neural network iteratively trains itself to find the optimal weights, how it verifies the model, and finally, how it stores the appropriate problem-specific neural network.
Figure 2B:
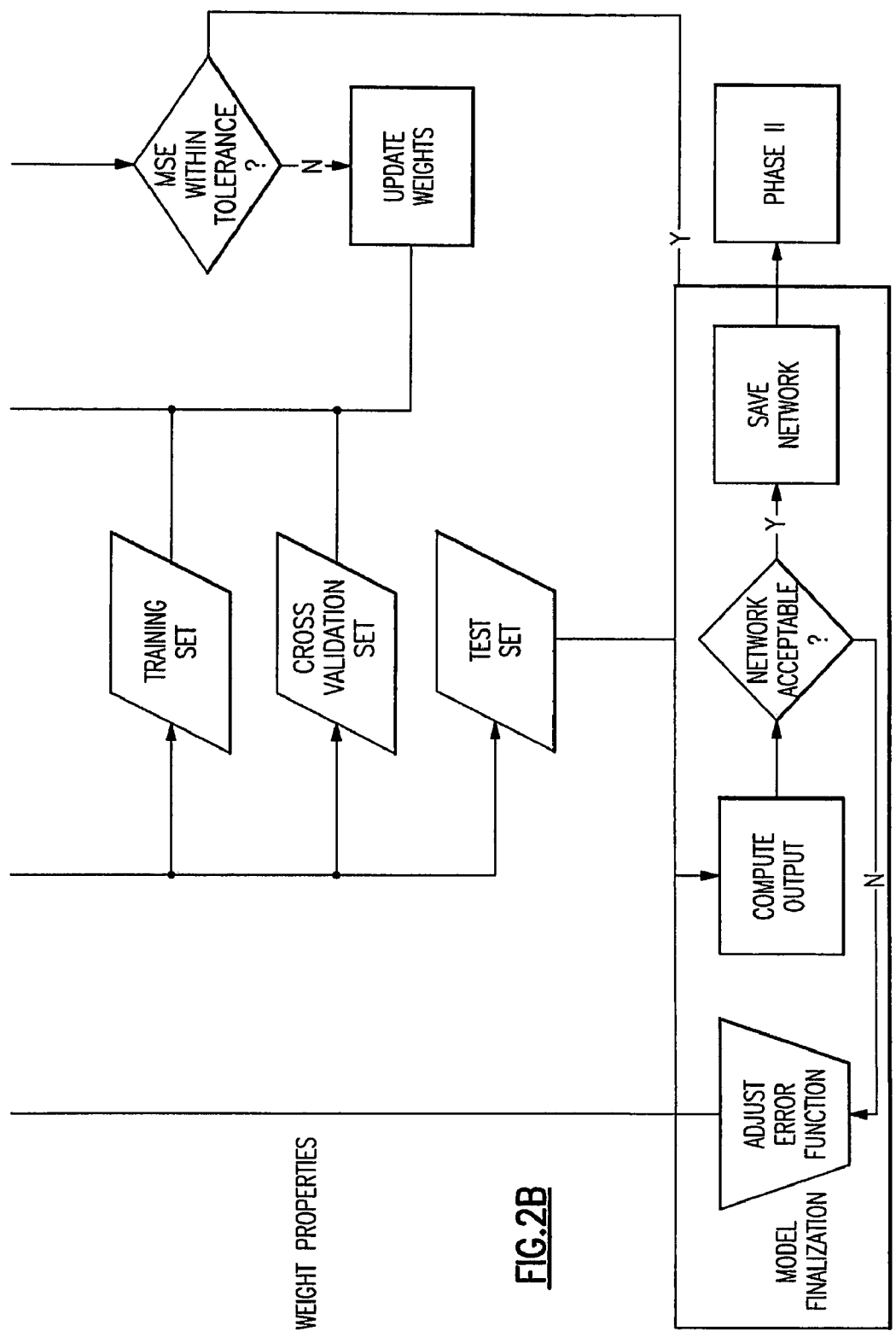
Figure 3A:
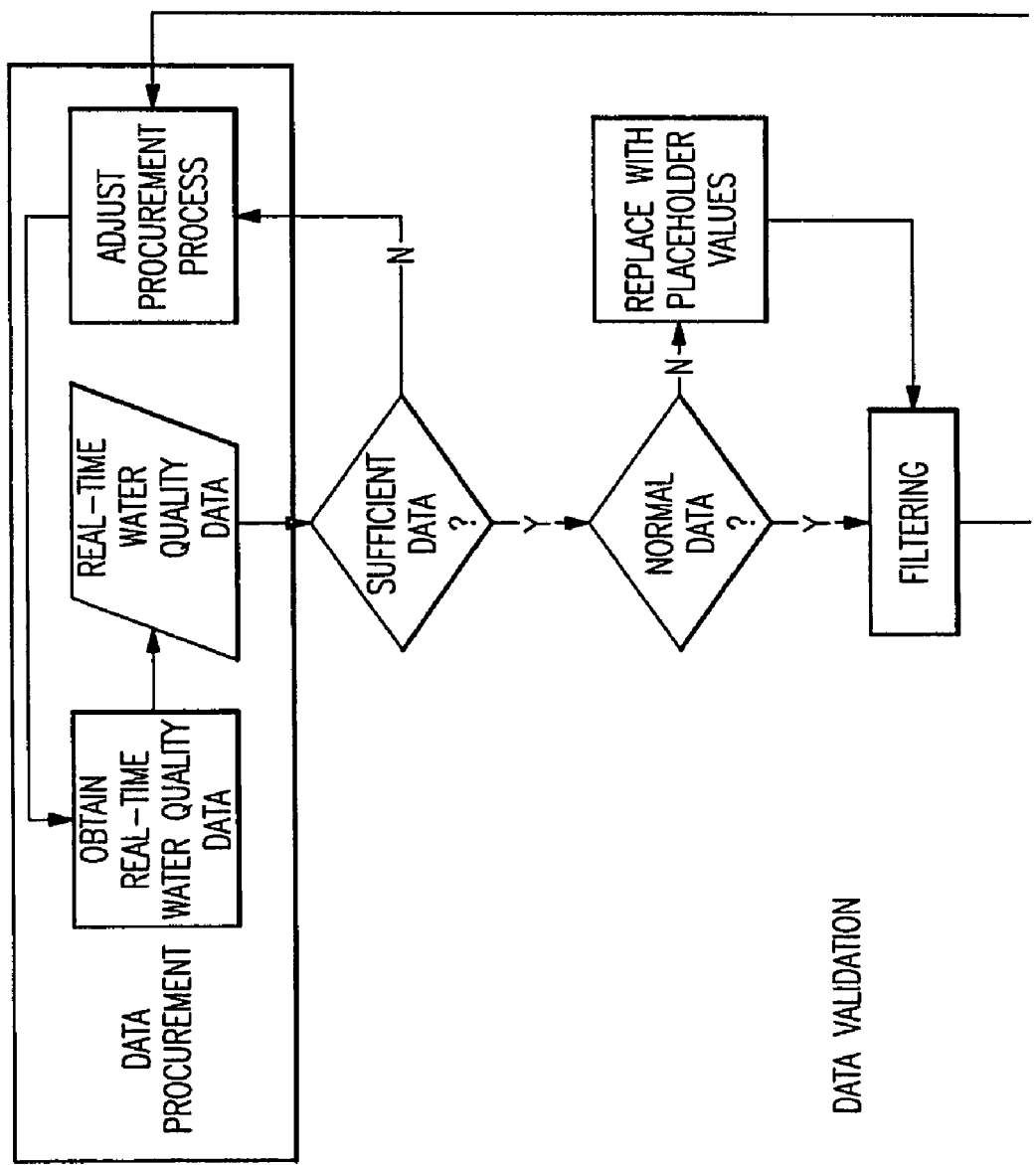
FIGS. 3a and 3b is a flow chart showing Phase II of neural network modeling, that is, the application of the model. This phase takes the saved neural network from the previous phase and uses procured data that is validated to detect and predict water quality conditions. Data validation encompasses checking the data for insufficiency, checking the data for abnormality, checking whether the data is historically justified and filtering random sensor noise.
Figure 3B:
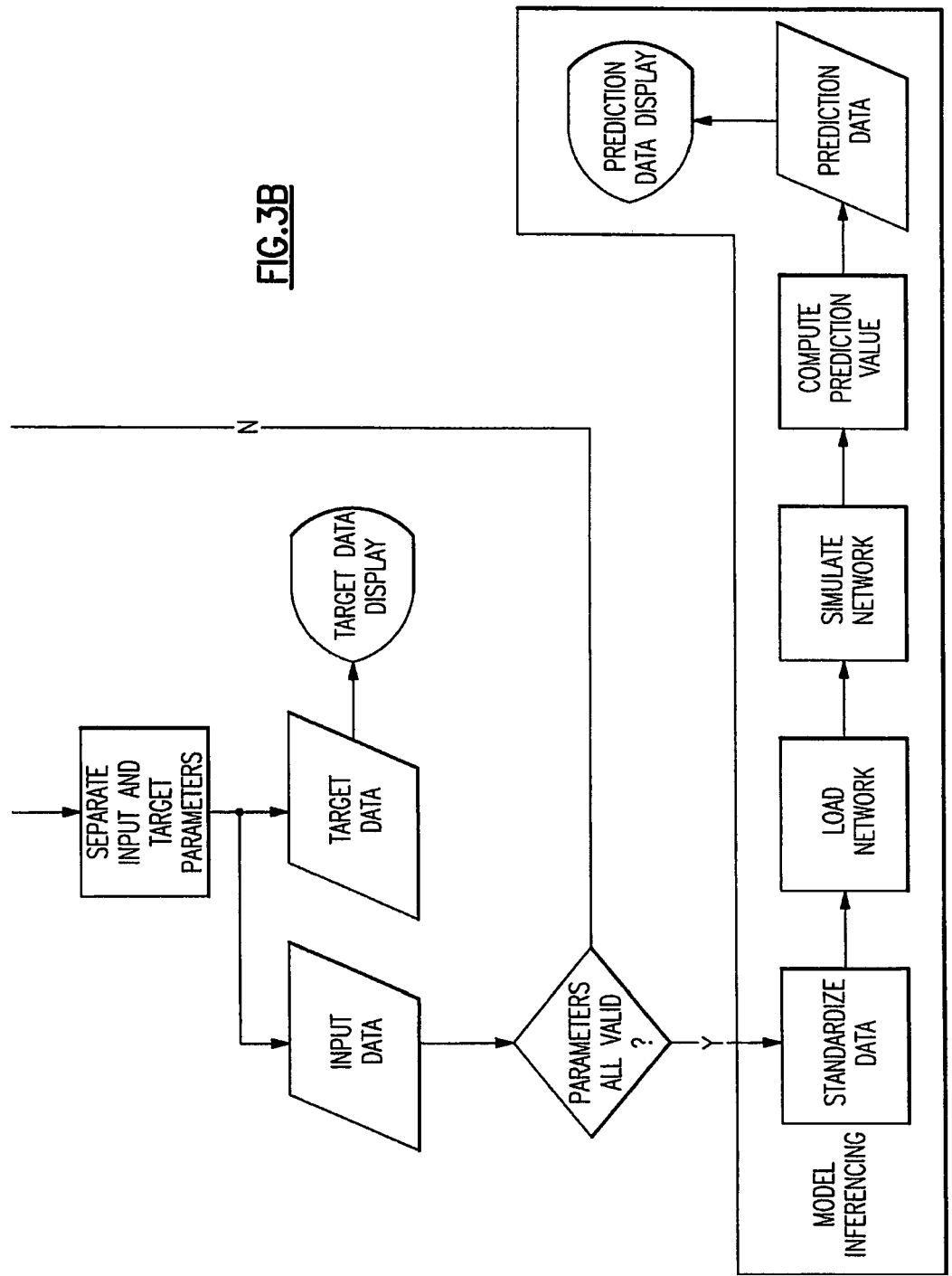

First, a neural network is modeled according to the algorithm shown as Phase I in FIGS. 2a and 2b, and then the neural network is applied according to the algorithm shown as Phase II in FIGS. 3a and 3b. Historical water quality data which is both location specific and in time series is obtained from a water source. The suite of water quality parameters that may be used as input parameters in the detection and prediction of water quality events may include any or all of the following and may not be limited to pH, temperature, dissolved oxygen, conductivity, turbidity, total chlorine, free chlorine, nitrite, ammonia, total organic carbon, chlorophyll, and phycocyanin. There must also be at least one target parameter, which is the parameter that is intended to be predicted. The historical water quality data is statistically preprocessed using correlation coefficient analysis, trend analysis, linear regression, if applicable, and a data normalization technique called standardization.

The correlation coefficient (R) is defined as $$R = \frac{c_{x_1 x_2}}{s_{x_1} s_{x_2}}, \tag{1}$$

where R is the correlation coefficient matrix and $c_{x_1 x_2}$ is the covariance between the variable $X_1$ and the variable $X_2$.

$$c_{x_1 x_2} = \frac{\sum_{i=1}^{n}(x_{1i} - \overline{x}_1)(x_{2i} - \overline{x}_2)}{n-1}, \tag{2}$$

where n is an integer and $\overline{x}$ is the mean vector of X. $S_{x_1}$ and $S_{x_2}$ are the standard deviation of the variable $X_1$ and $X_2$.

$$S_{x_1} = \sqrt{\frac{\sum_{i=1}^{n}(x_{1i} - \bar{x}_1)^2}{n-1}}, S_{x_2} = \sqrt{\frac{\sum_{i=1}^{n}(x_{2i} - \bar{x}_2)^2}{n-1}}. \quad (3)$$

A correlation coefficient between 0 and 0.30 is generally defined as "weak," a correlation coefficient between 0.30 and 0.60 as "moderate," a correlation between 0.6 and 0.90 as "strong," and a correlation of 1.00 as "perfect." A negative sign indicates an inverse relationship between the two parameters whereas a positive sign indicates a direct relationship between the two parameters.

In linear regression analysis, the two sets of water quality parameters, the input parameter set and the target parameter set, are checked for linearity. If the nature of the relationship between the input water quality parameters and the target water quality parameter(s) shows characteristics of linearity, then linear regression modeling techniques are appropriate. For example, a straight-line relationship can be valuable in summarizing the observed dependence of one variable on another. The equation of such a straight line can be obtained by the method of least squares when data are available. The linear first-order model can be written $$Y = \beta_0 + \beta_1 X + \epsilon; \quad (4)$$

that is, for a given matrix X, a corresponding observation vector Y can be modeled by $\beta_0 + \beta_1 X$ plus an error term $\epsilon$, the increment by which any individual Y may fall off the regression line. $\beta_0$ is the intercept of Y. $\beta_1$ is a vector of regression coefficients. $\beta_0 + \beta_1 X$ is the model function, and $\beta_0$ and $\beta_1$ are called the parameters of the model. Here $\beta_0$, $\beta_1$, and $\epsilon$ are unknown, and in fact $\epsilon$ would be difficult to discover since it changes for each observation Y.

However, $\beta_0$ and $\beta_1$ remain fixed and, although they cannot be found exactly without examining all possible occurrences of Y and X, $\beta_0$ and $\beta_1$ can be estimated with $b_0$ and $b_1$ using finite data.

$$\hat{Y} = b_0 + b_1 X, \quad (5)$$

where $\hat{Y}$ is the predicted value for a given X. As such, $b_0$ and $b_1$ are determined by minimizing the squared errors. Suppose there is available n sets of observations $(X_1, Y_1)$, $(X_2, Y_2)$, $(X_3, Y_3)$, ..., $(X_n, Y_n)$. Then by equation (4) it can be written that $$Y_i = \beta_0 + \beta_1 X_i + \epsilon_i, \quad (6)$$

for i=1, 2, ..., n, so that the sum of squares of deviation from the rule line is $$S = \sum_{i=1}^{n} \epsilon_i^2 = \sum_{i=1}^{n}(Y_i - \beta_0 - \beta_1 X_i)^2. \quad (7)$$

S is called the sum of squares function. The vectors $b_0$ and $b_1$ can be determined by differentiating equation (7) first with respect to $\beta_0$ and then with respect to $\beta_1$ and setting the results equal to zero.

$$\frac{\partial S}{\partial \beta_0} = -2\sum_{i=1}^{n}(Y_i - \beta_0 - \beta_1 X_i) \quad (8)$$

and $$\frac{\partial S}{\partial \beta_1} = -2\sum_{i=1}^{n} X_i(Y_i - \beta_0 - \beta_1 X_i),$$

so that the estimates $b_0$ and $b_1$ are solutions of the two equations $$\sum_{i=1}^{n}(Y_i - b_0 - b_1 X_i) = 0 \quad (9)$$

and $$\sum_{i=1}^{n} X_i(Y_i - b_0 - b_1 X_i) = 0,$$

where $(b_0, b_1)$ is substituted for $(\beta_0, \beta_1)$ and equation (8) is equated to zero. From equation (9), $$b_0 n + b_1 \sum_{i=1}^{n} X_i = \sum_{i=1}^{n} Y_i, \quad (10)$$

$$b_0 \sum_{i=1}^{n} X_i + b_1 \sum_{i=1}^{n} X_i^2 = \sum_{i=1}^{n} X_i Y_i.$$

These equations are called the normal equations.

$$b_1 = \frac{c_{xy}}{S_x^2} = \frac{\sum(X_i - \bar{X})(Y_i - \bar{Y})}{\sum(X_i - \bar{X})^2} \quad (11)$$

and $$b_0 = \bar{Y} - b_1 \bar{X} \quad (12)$$

for intercept at X=0. Substituting equation (12) into equation (5) gives the estimated regression equation in the alternative form $$\hat{Y} = \bar{Y} + b_1(X - \bar{X}). \quad (13)$$

When there is no linearity, non-linear modeling techniques like neural networks are appropriate. Neural networks contain input neurons which receive any number of inputs and each of these inputs is assigned a weight, which governs the strength of the signal. Like biological systems, each neuron also has a single threshold value. The neuron is activated by adding the weighted sum of the inputs and subtracting the threshold value. This activation signal is then applied to a transfer function, like a hard limit, sigmoidal, or linear function, to produce the output of the neuron. A hard limit function passes negative information when the output is less than the threshold and positive information when the output is greater than or equal to the threshold. A sigmoidal function is a continuous function that varies gradually between two asymptotic values, typically 0 and 1, or −1 and +1. A linear function calculates the neuron's output by simply returning the value passed to it. The transfer function allows the network to carry out non-linear interpolations to compose a reasonable output signal from the range of input signals.

Accordingly, this type of function can evaluate the non-linear sets of input parameters that exist when determining water quality events.

Water quality data is measured in different scale units; therefore, a data normalization technique like standardization is needed to reduce the scale variation that exists. Standardization reduces this variation found in different scales to standardized scales while maintaining the dynamics of the data. Standard z-score (Z) is defined as $$z_i = \frac{x_i - \bar{x}}{S_x}, \tag{14}$$

where $\bar{x}$ is the mean vector of X and $S_x$ is the standard deviation of X. $z_i$ is the standard score for the ith observation. The statistical results of standardization are the mean of z ($\bar{z}$)=0 and standard deviation of z ($S_z$)=1. Having the standardized mean equal to zero implies that any differences in the mean values of the water quality data will be mitigated. Distortions stemming from these differences will be eliminated in the same way the differences in scale are eliminated. By having the standard deviation limited to one, this makes sure that the effect of differently scaled data is neither magnified nor attenuated more than necessary. As will be explained below, this type of standardized data will not cause the weights to be greatly maladjusted during the training period so that the relationship between the input and the target parameters is distorted, which can then reduce the performance of the network or even render it less robust.

Neural networks come in various architectural models such as radial basis, backpropagation, generalized regression, probabilistic, Elman, and Hopfield network models. In this particular embodiment of the invention, a Levenberg-Marquardt (LM) network model is adapted: both phases of applications in this invention, phase I of neural network modeling as well as phase II of neural network application, utilize the Levenberg-Marquardt optimization algorithm (LMOA). The LMOA is an iterative technique that locates the minimum of a function that is expressed as the sum of squares of nonlinear functions. With each parameter represented as a nonlinear function, this becomes useful in solving the nonlinear least-squares problem that is presented. The number of parameters to be solved by the LMOA is kept as few as possible to create the least amount of error in the iteration process. The LMOA is an accurate learning algorithm that can handle nonlinear parameter identification, and a good starting estimation of the unknown parameters is needed in order to achieve convergence in a timely manner.

Figure 5:
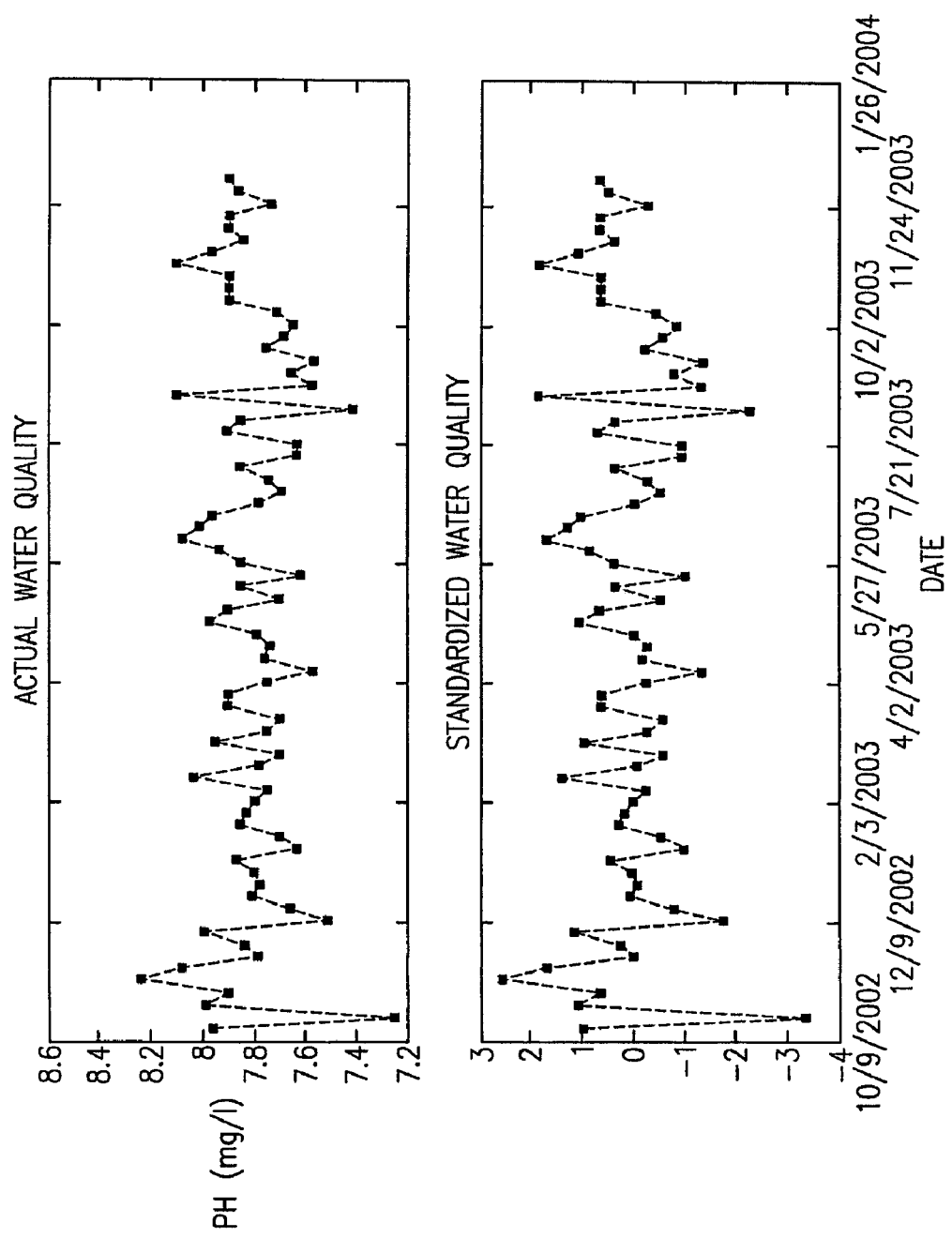
FIG. 5 are two graphs, the first of which is the actual water quality data plot for pH of a water sample over a period of time (top) and the second of which is the standardized water quality data plot for pH of the water sample over the same period of time (bottom).
Figure 7:
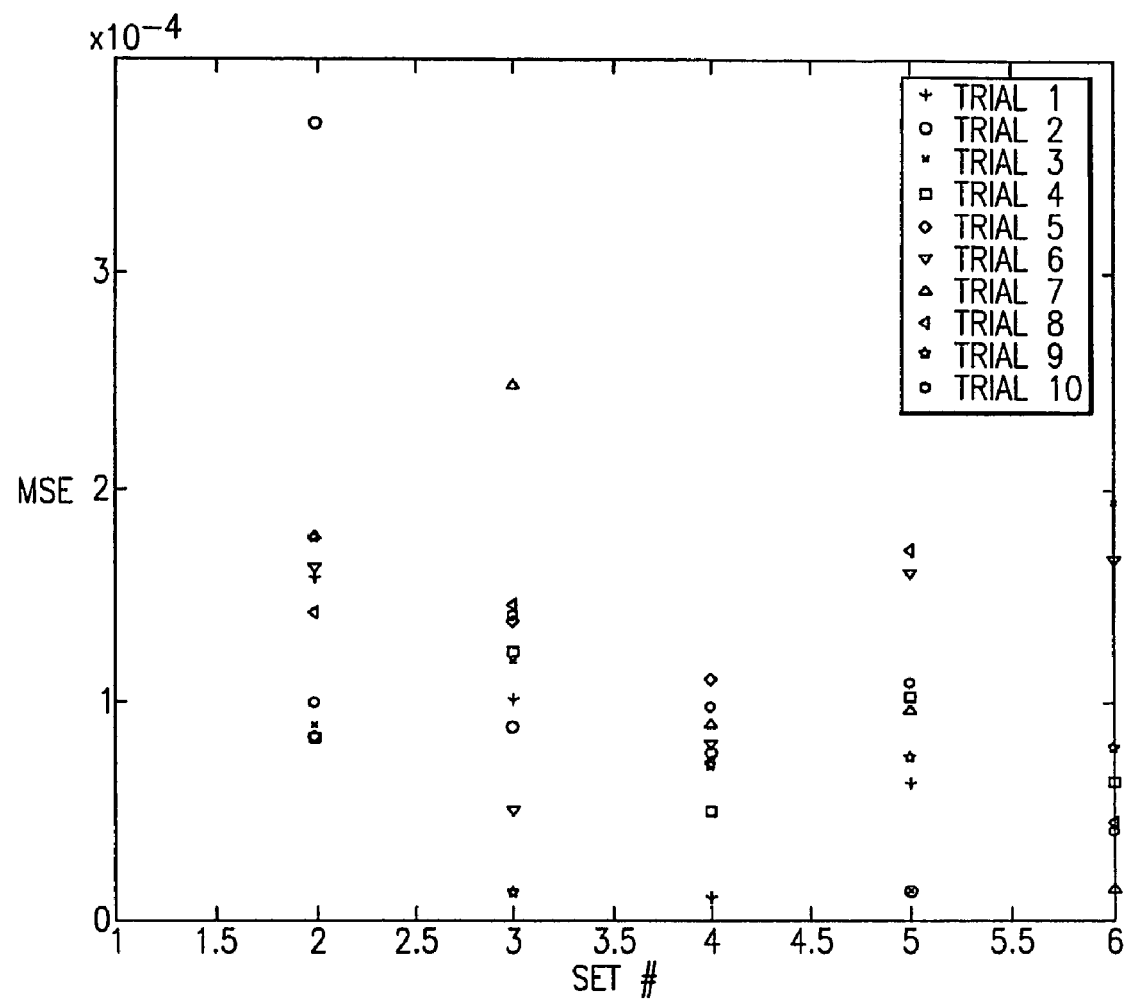
FIG. 7 is a graph of the mean squared errors (MSE) that were calculated with two neurons and ten trials for five different time delay periods in the nitrification example.

Let a function ($f$) be an assumed functional relation which maps a weight vector w∈$R^m$ to an estimated target vector $\hat{Y}$=$f$(w), $\hat{Y}$∈$R^n$. Hence, n≥m. An initial weight estimate $w_0$ and a target vector Y are provided and it is desired to find the vector $w_{optimal}$ that best satisfies the functional relation $f$, i.e. minimizes the squared distance $\epsilon^T\epsilon$ with $\epsilon$=Y-$\hat{Y}$. The mean squared error (MSE) is the mean of $(Y-\hat{Y})^2$. FIGS. 5 and 7 show example MSEs calculated by the nitrification time delay program. The basis of the LM algorithm is a linear approximation to $f$ in the neighborhood of w. For a small $\|\delta_w\|$, a Taylor series expansion leads to the approximation $$f(w+\delta_w) \approx f(w) + J\delta_w, \tag{15}$$

where J is the Jacobian matrix $$\frac{\partial f(w)}{\partial w}.$$

LM initiates at the starting point $w_0$ and the method produces a series of vectors $w_1, w_2, \ldots$, that converge towards a local minimizer $w_{optimal}$ for $f$. Hence, at each step, it is required to find the $\delta_w$ that minimizes the quantity $$\|Y-f(w+\delta_w)\| \approx \|Y-f(w)-J\delta_w\| = \|\epsilon - J\delta_w\|. \tag{16}$$

The sought $\delta_w$ is therefore the solution to a linear least-squares problem: the minimum is attained when $J\delta_w - \epsilon$ is orthogonal to the column space of J. This leads to $$J^T(J\delta_w - \epsilon) = 0, \tag{17}$$

which yields to $$J^T J\delta_w = J^T \epsilon. \tag{18}$$

The matrix $J^T J$ in the left hand side of equation (18) is called the approximate Hessian, i.e. an approximation to the matrix of second order derivatives. The LM method actually solves a slight variation of equation (18), known as the augmented normal equation $$N\delta_w = J^T \epsilon. \tag{19}$$

where the off-diagonal elements of N are identical to the corresponding elements of $J^T J$ and the diagonal elements are given by $$N_{ii} = \mu I + [J^T J]_{ii} \tag{20}$$

for some μ>0. The LM algorithm uses this approximation to the Hessian matrix in the following Newton-like update:

$$Y_{k+1} = Y_k - [J^T J + \mu I]^{-1} J^T \epsilon. \tag{21}$$

In equation (21), when the scalar μ is zero, this is just Newton's method, using the approximate Hessian matrix. When μ is large, this becomes gradient descent with a small step size. Newton's method is faster and more accurate near an error minimum, so the aim is to shift towards Newton's method as quickly as possible. Thus, μ is decreased after each successful step (reduction in the mean of $\epsilon^T\epsilon$) and is increased only when a tentative step would increase the error function. In this way, the error function will always be reduced at each iteration of the algorithm, until the minimization of the error function (MSE) is achieved, at which point, the algorithm terminates. The MSE and $R^2$ calculations enable the performance of the model to be assessed.

Figure 14:
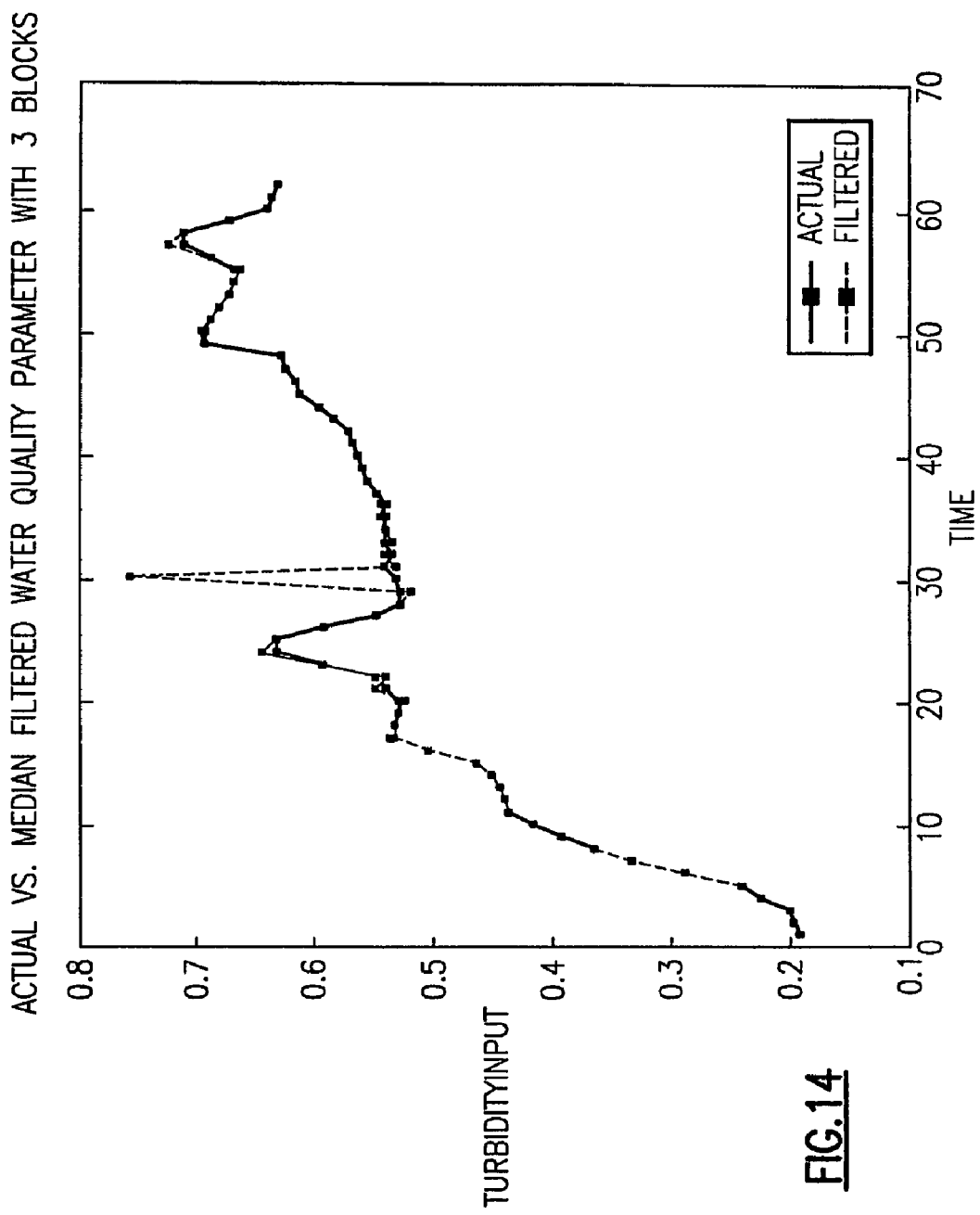
FIG. 14 is a graph showing plots of actual data and filtered data.

After modeling of the neural network is complete, real-time water quality data is obtained for the application phase of the system (Tier 1 of FIGS. 3a and 3b). This data is evaluated in three ways, to check for insufficiency, abnormality, and invalidity (Tier 2 of FIGS. 3a and 3b). Insufficient data is data in which the amount of data is inadequate to provide a prediction value for the target parameter. As stated earlier, data must be location specific and in time series, and this time series data must span at least a minimum length of time and include a complete set of values for all the water quality parameters of interest. If the data is insufficient, the system allows for the procurement period to lengthen until sufficient data is obtained. Abnormal data is data in which the type of data is inadequate to provide a prediction value for the target parameter. These types of data values include negative numbers or values that are not numbers. If the data is abnormal, they are replaced with placeholder values. The data could still include random sensor noise. To minimize sensor noise, the system can include refining the data, e.g., by using a median filtering method (see, for example, FIG. 14). Then the data is separated into input and target parameters, with the target parameter(s) displayed for the user. The input water quality data is then evaluated for validity, that is, checked to see how it compares to the historical water quality data that was used in modeling the neural network. If the real-time water quality data is outside a certain range that is determined by the data that was obtained in the past, then the user is prompted of this fact.

Filtering data, if employed, can be accomplished using any suitable filtering method. Persons of skill in the art are familiar with, and have access to, a wide variety of filtering methods, and any of such methods can, if desired, be employed. For example, one type of filtering method is median filtering—persons skilled in the art are familiar with such methods, and have easy access to such methods and devices which can perform such methods. Where median filtering is employed, any desired number of blocks can be used, e.g., from 2 to 17 blocks, such as 3 blocks.

After the real-time water quality input data is validated, the neural network computes a prediction value based on the input parameters (Tier 3 of FIGS. 3a and 3b). To do this, the data is normalized in the same standardization technique that was used for the historical water quality data. The neural network is then loaded with the properties of the model that were determined in the previous phase. Using this architecture, the network is simulated with the new inputs to compute a prediction value. This prediction value, as with the detection value, is also displayed for the user.

TABLE 1

| Variable | Definition |
| --- | --- |
| X | Input vector |
| $\bar{X}$ | Mean input vector |
| $\beta_0$ | Bias vector |
| $\beta_1$ | Regression coefficient vector |
| $b_0$ | Predicted bias vector |
| $b_1$ | Predicted regression coefficient vector |
| S | Sum of squares function |
| $S_x$ | Standard deviation of X |
| $S_z$ | Standard deviation of Z |
| $R^m$ | m-tuple set of real numbers |
| $R^n$ | n-tuple set of real numbers |
| Y | Target vector |
| $\hat{Y}$ | Estimated target vector |
| $\bar{Y}$ | Mean target vector |
| w | Weight vector |
| $w_0$ | Initial weight vector |
| $w_{optimal}$ | Optimal weight vector |
| $\delta_w$ | Incremental weight change |
| J | Jacobian matrix |
| $J^T$ | Transposed Jacobian matrix |
| N | Hessian matrix |
| μ | Damping term |
| ε | Error matrix |
| $\epsilon^T$ | Transposed error matrix |
| R | Correlation coefficient |
| C | Covariance matrix |
| Z | Standard z-score matrix |
| $\bar{z}$ | Mean z-score matrix |

TABLE 2

| Acronym | Name |
| --- | --- |
| WQCIE | Water Quality Control Inference Engine |
| MIB | 2-methylisoborneol |
| TTHM | Total Trihalomethanes (total of 4) |

TABLE 2-continued

| Acronym | Name |
| --- | --- |
| HAA5 | Haloacetic Acids (total of 5) |
| DO | Dissolved Oxygen |
| TOC | Total Organic Carbon |
| LM | Levenberg-Marquardt |
| LMOA | Levenberg-Marquardt Optimization Algorithm |
| DBP | Disinfectant Byproduct |
| MSE | Mean Squared Error |

EXAMPLE

Samples

Water quality data for nine parameters obtained from a single water source in time series were used in the detection and prediction of nitrification. These parameters included input parameters pH, temperature, DO, conductivity, turbidity, total chlorine, ammonia, and TOC, and the target parameter, nitrite. The data was collected periodically over the course of one year and five months from a single municipal water source.

Methods

Figure 6:
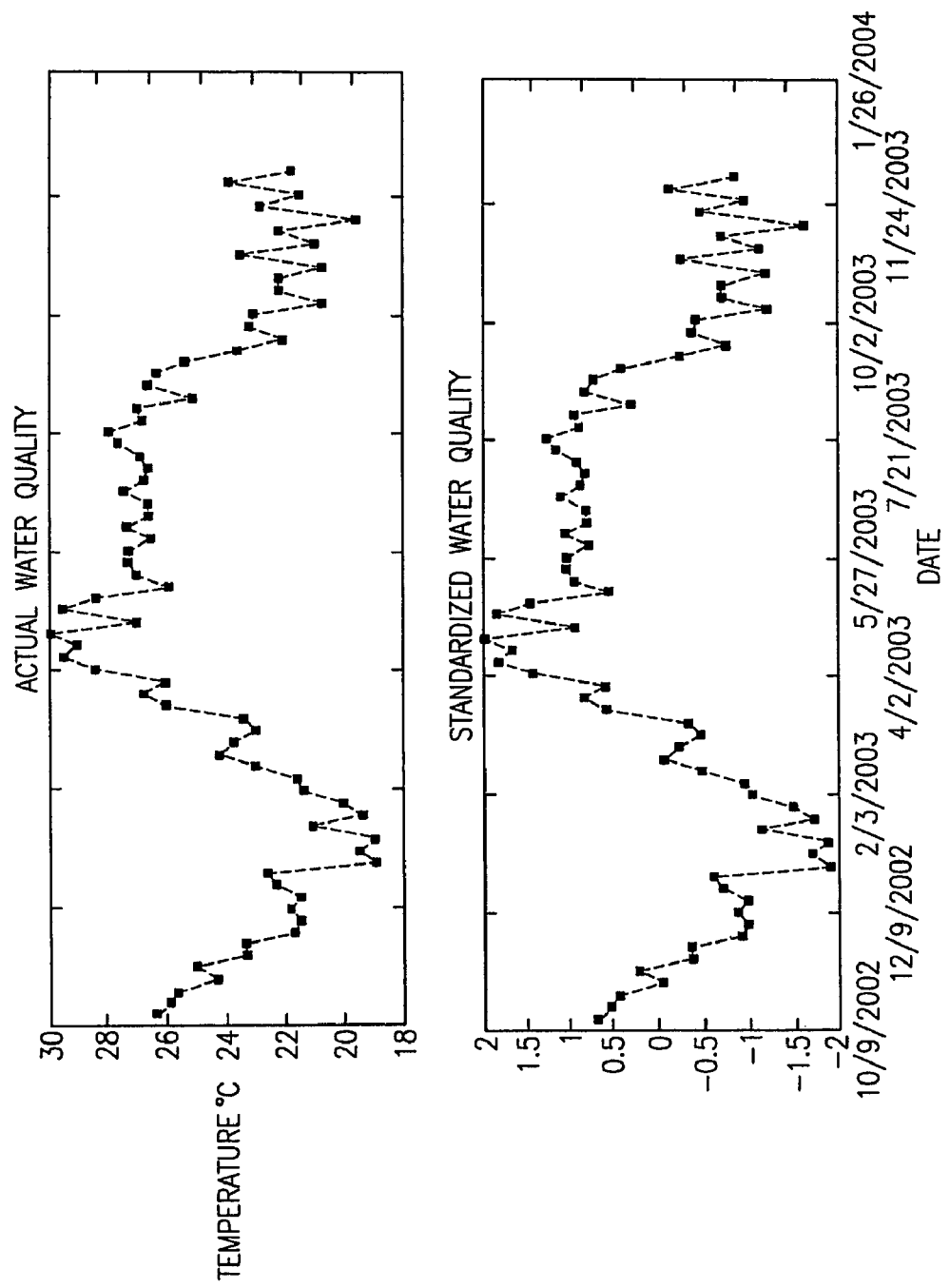
FIG. 6 includes two graphs, the first of which is the actual water quality data plot for temperature of a water sample over a period of time (top) and the second of which is the standardized water quality data plot for temperature of the water sample over the same period of time (bottom).

First, historical water quality data for nine parameters as defined above were obtained (Tier 1 of FIGS. 2a and 2b). The statistical preprocessing techniques applied in this example included correlation coefficient analysis, trend analysis, and standardization (Tier 2 of FIGS. 2a and 2b). FIG. 4 shows the results from the correlation coefficient analysis. All the correlation coefficients that were calculated between different water quality parameters were moderate or weak (R<0.6). As expected, the correlation coefficient between any parameter and itself was perfect or equal to 1.00, while the correlation coefficient between two different parameters varied; for example, the correlation coefficient between pH and temperature was −0.03 and the correlation coefficient between pH and conductivity was 0.07. Furthermore, linearity was checked between input and target parameters, and it was found that no such dependency existed. All the scales of the data were then standardized. FIGS. 5 and 6 show the actual and standardized data plots of two water quality parameters, pH and temperature. Note that, while the scale of the data plot changed, the dynamics of the data were maintained.

Figure 8:
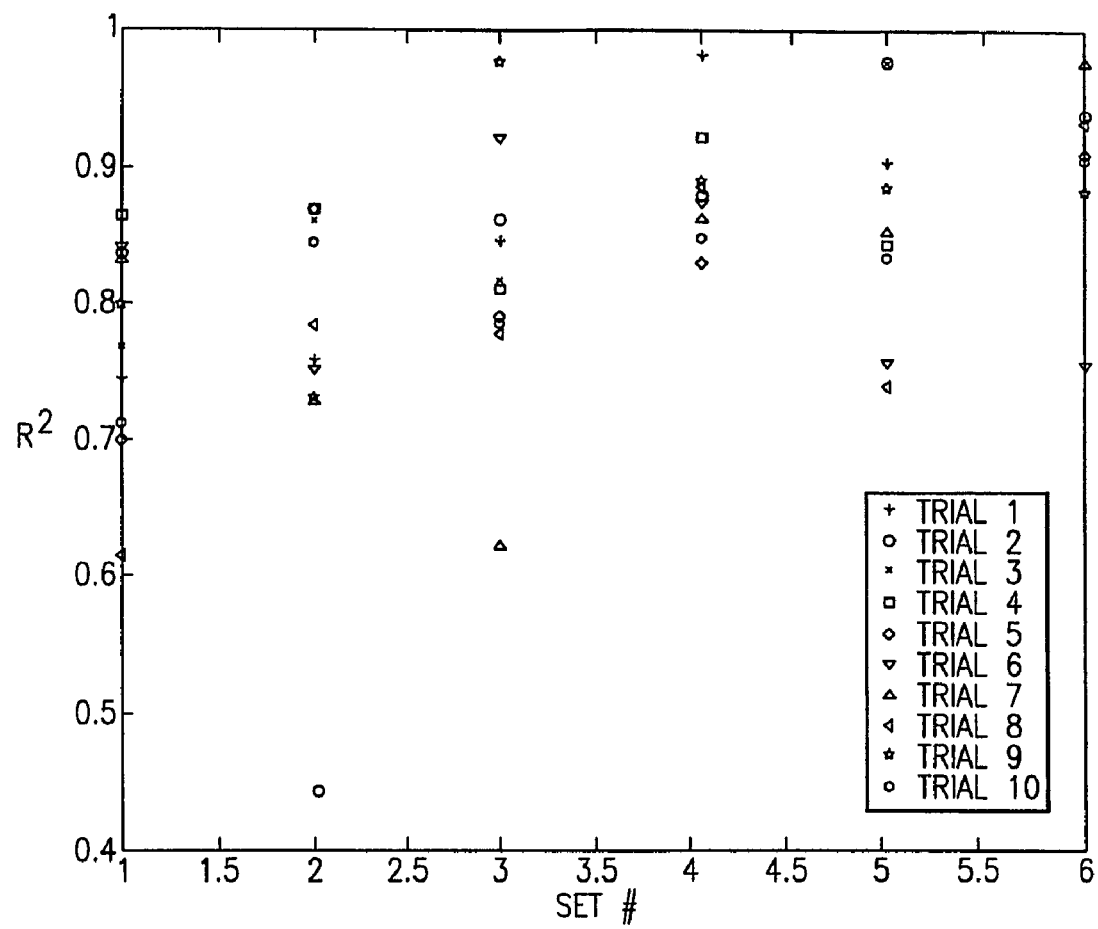
FIG. 8 is a graph of the squared correlation coefficients ($R^2$) that were calculated with two neurons and ten trials for five different time delay periods in the nitrification example.
Figure 9:
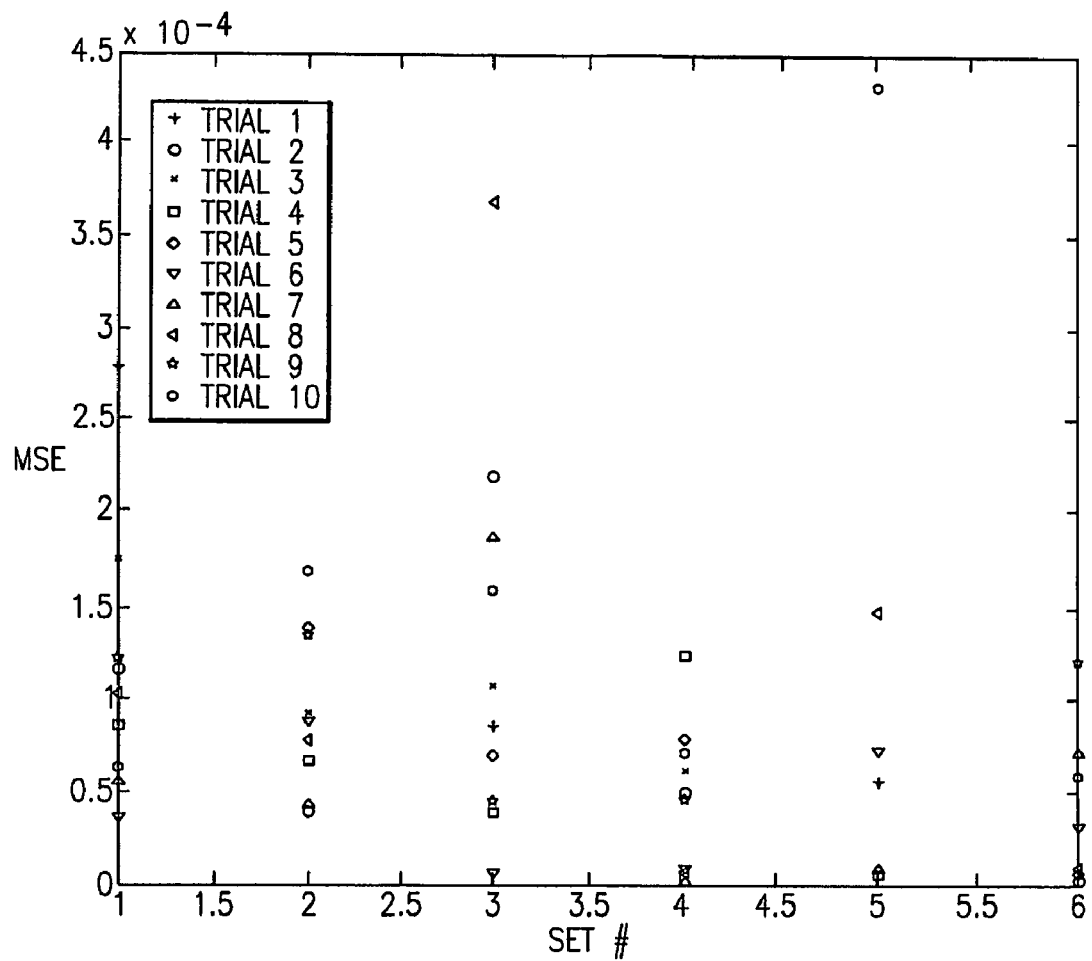
FIG. 9 is a graph of the MSE calculations with three neurons and ten trials for five different time delay periods in the nitrification example.
Figure 10:
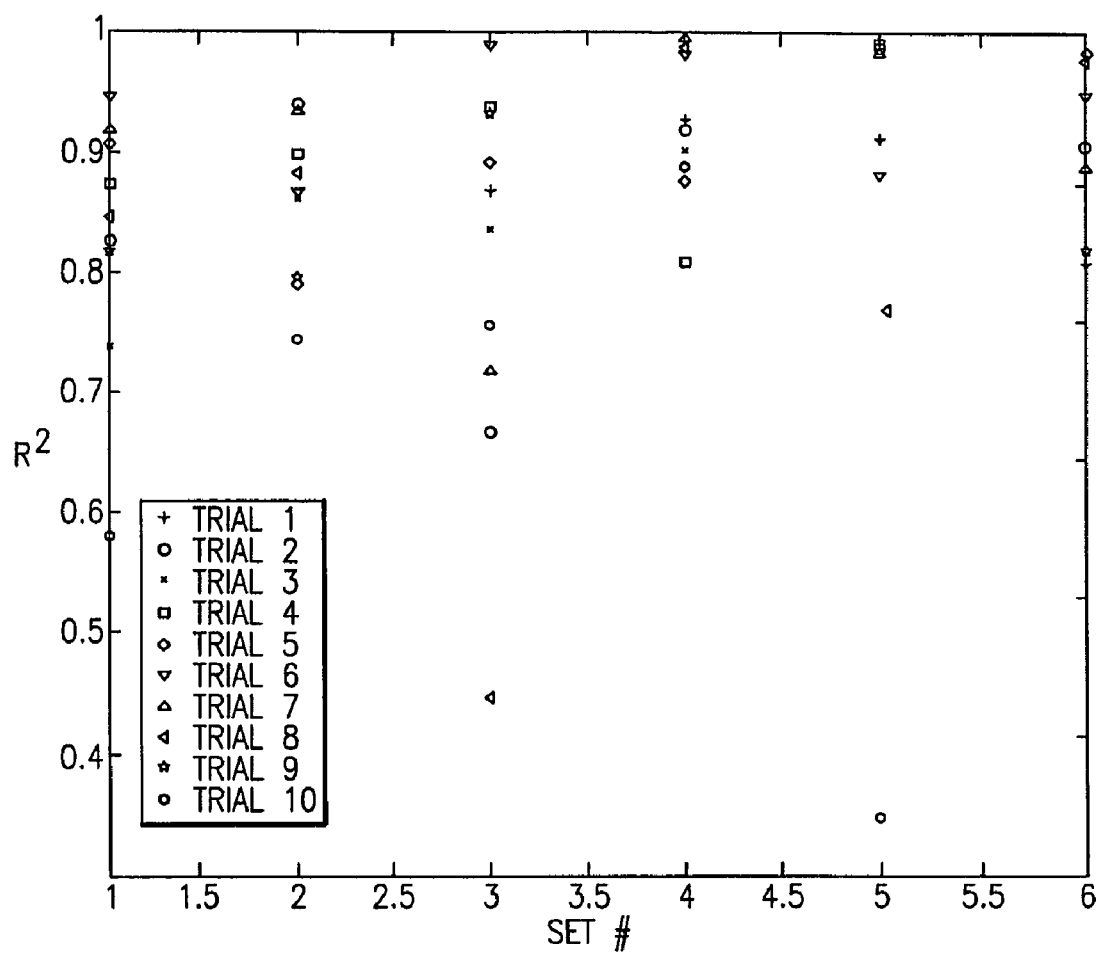
FIG. 10 is a graph of the $R^2$ calculations with three neurons and ten trials for five different time delay periods in the nitrification example.
Figure 11:
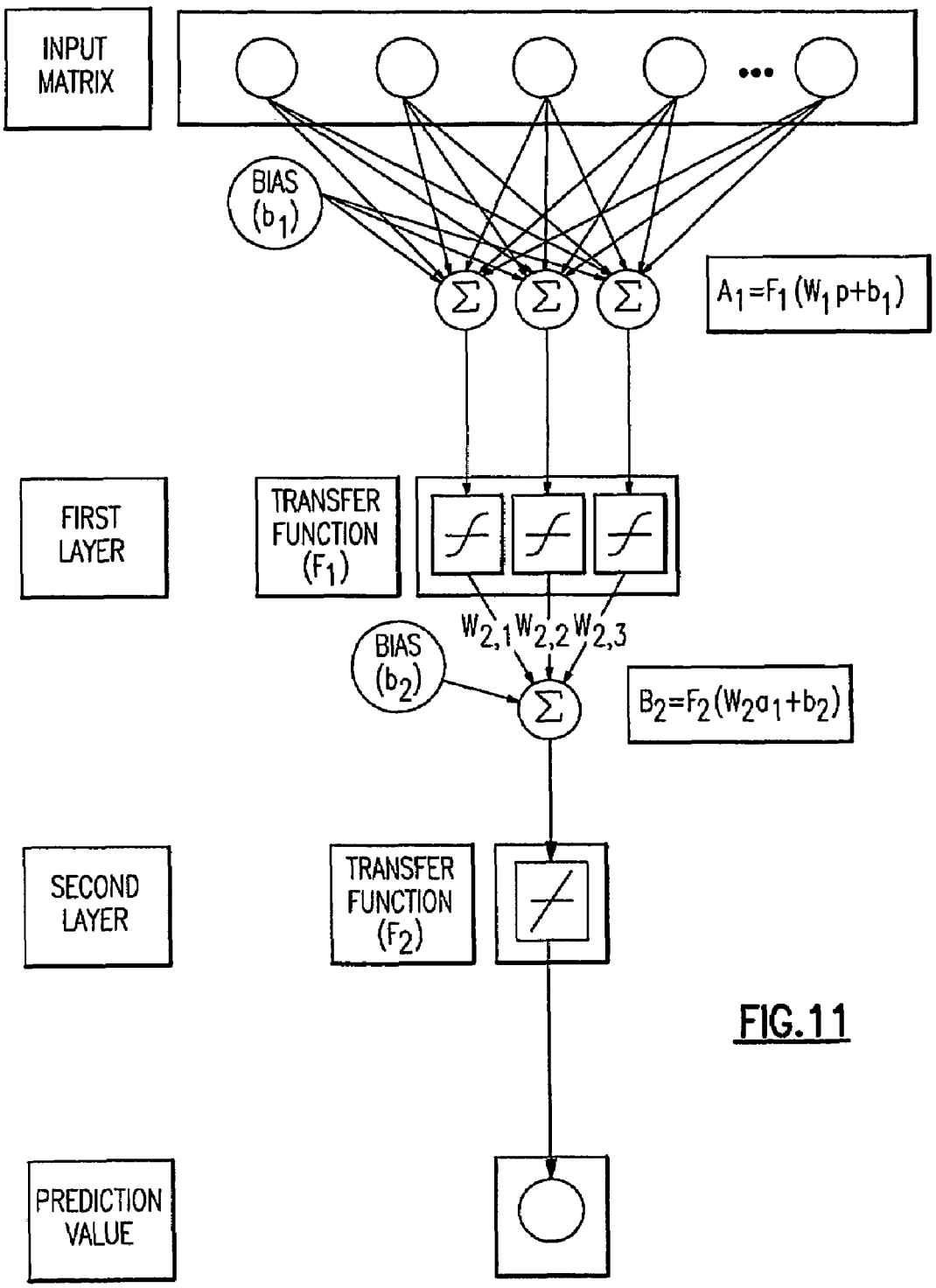
FIG. 11 is a schematic diagram of the architecture of the neural network model.

After the data preprocessing was completed, two critical properties of the model, the optimal neuron number and optimal time delay period, were determined (Tier 3 of FIGS. 2a and 2b). To do this, the time delay application created a number of different sequential time delay periods to find the most probable time delay period for nitrification and incrementally ran the LM algorithm starting with two neurons all the way up to fifteen neurons to find the optimal number of neurons to use for nitrification prediction. FIGS. 7 and 8 show the MSE and $R^2$ calculations between actual nitrite values and estimated nitrite values using two neurons with ten trials for five different time delay periods, while FIGS. 9 and 10 show the MSE and $R^2$ calculations using three neurons with ten trials for five different time delay periods. Through this process, the optimal number of neurons to use in the neural network and the most probable period of time delay that led to the best possible prediction performance, i.e. the lowest MSE and highest $R^2$, for the nitrification model were determined. Modeling of the neural network resulted in an architecture depicted in FIG. 11.

Figure 12:
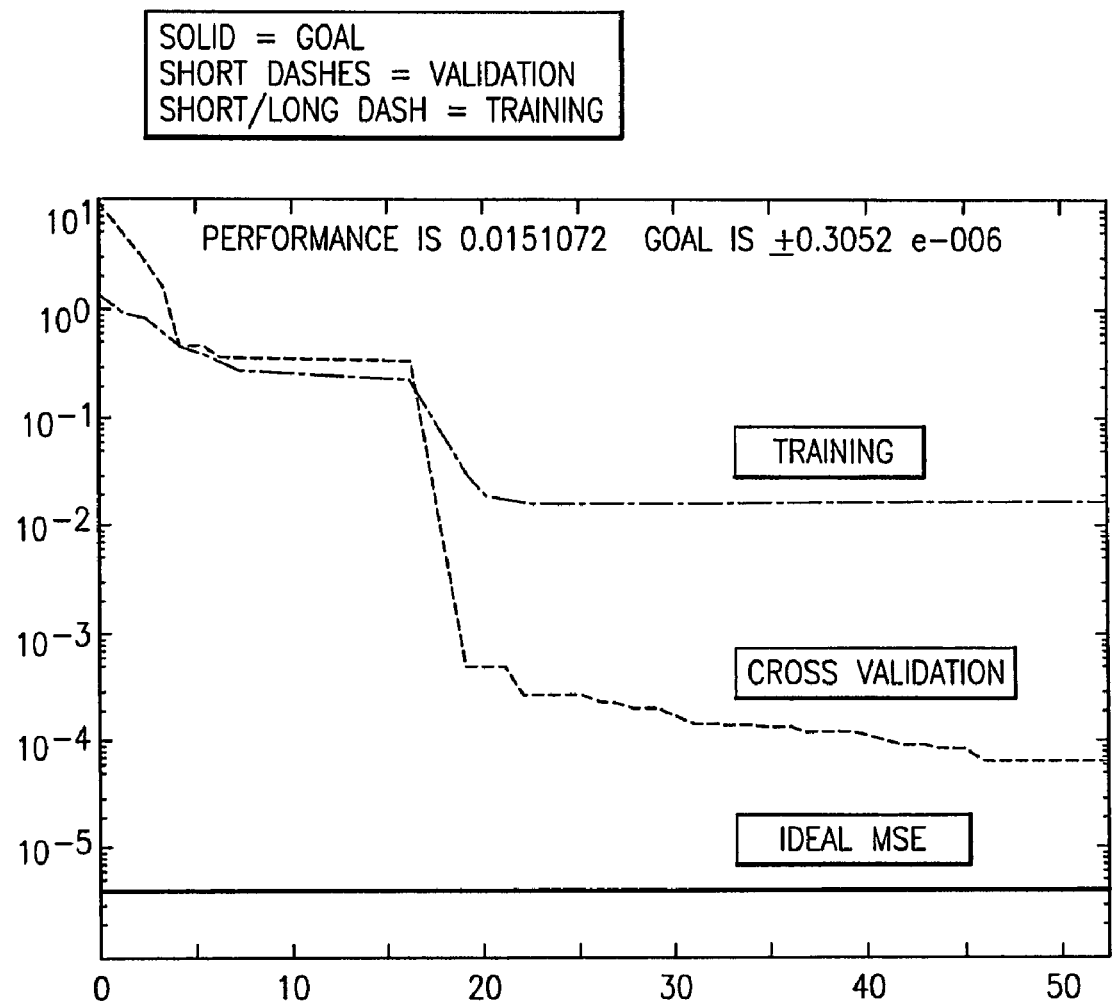
FIG. 12 is a graph showing the error function minimization. The blue line represents the training set, the green line represents the cross validation set, and the black line represents the ideal value for MSE that the model wants to achieve.
Figure 13:
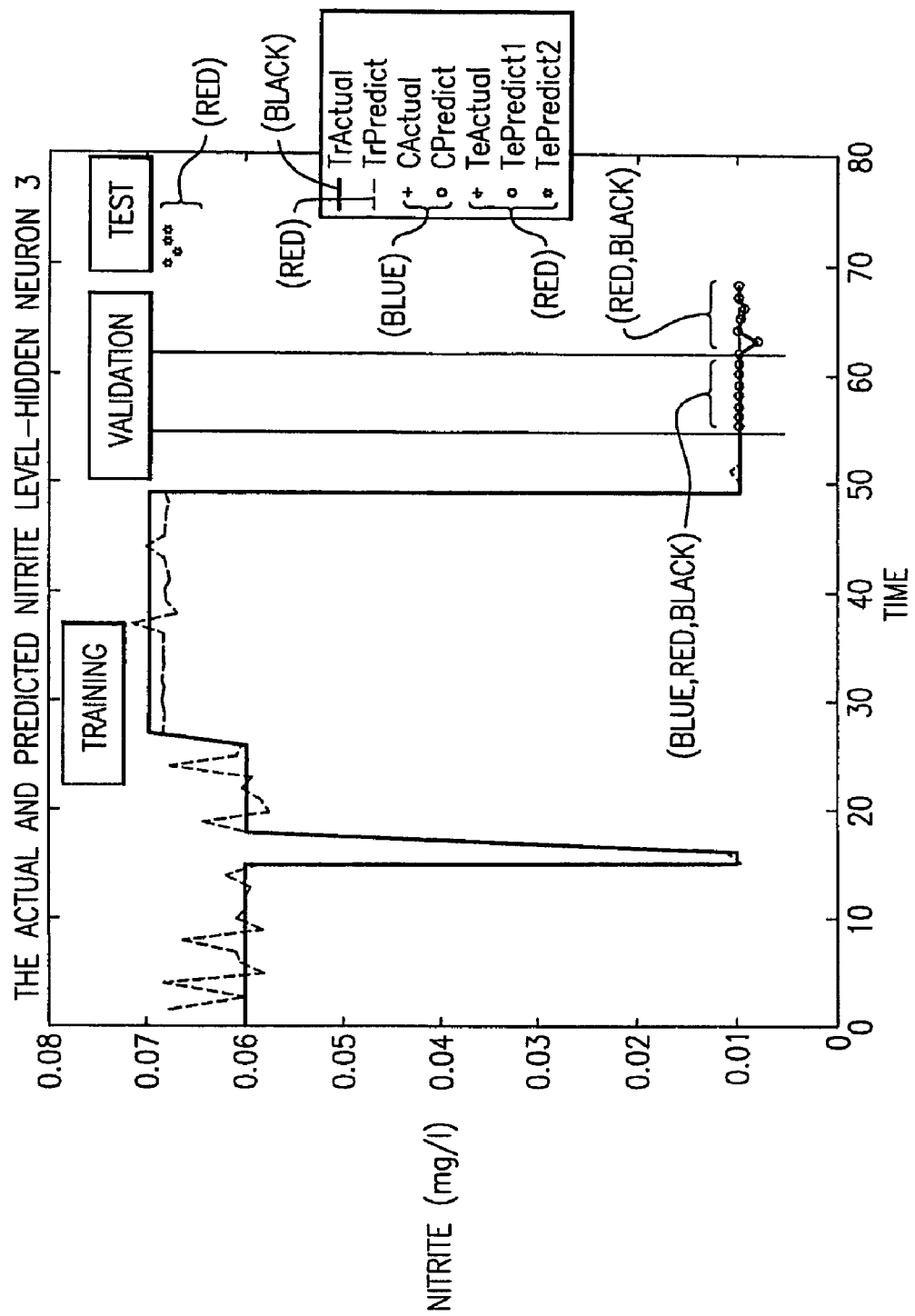
FIG. 13 is a graph showing how the neural network model is generated by separating the data into three data sets: training, cross validation, and testing sets.

The inferencing program then automatically divided the data into three sets, a training set, a cross validation set, and a test set. The training set was used to learn the patterns between the input parameters and the target parameter (nitrite). To learn the patterns, it adjusted the weights assigned to the input values in such a way that the error function was minimized. The cross validation set was used to avoid overfitting, a general problem encountered in regression modeling, which may have resulted during the training period. This iterative process in determining the weight properties is illustrated in the fourth tier of FIGS. 2a and 2b. The inferencing program continued to compute the output with updated weights until the MSE minimization reached a tolerable threshold. FIG. 12 shows how well the error function was minimized using the training and cross validation sets of data. The test set was then used to compare actual nitrite values with the estimated nitrite values, the latter of which were generated by the built-in relationship as determined by the training and cross validation steps. This verification of the network is illustrated in the fifth tier of FIGS. 2a and 2b and how well it accomplished this is shown in FIG. 13.

Results

This representative system in accordance with the present invention utilized the input parameters from this particular municipal water supply to determine an optimal neuron number of three for the nitrification model and an optimal proliferation time period of 26 days for nitrification prediction. Using this time delay period and number of neurons, the squared correlation coefficient between actual nitrite values and estimated nitrite values ended up being 0.98. When supplied with subsequent real-time data values, the neural network was able to correctly predict the onset of nitrification this many days in advance.

Whereas particular aspects of the method of this invention and particular embodiments of the invention have been described for purposes of illustration, it will be appreciated by those skilled in the art that numerous variations of the details may be made without departing from the invention as described in the appended claims.

What is claimed is:

1. A method of evaluating water samples for the possible future presence of a water quality event, comprising:
    obtaining a plurality of water quality data over a period of time, wherein the data comprises values for water quality parameters,
    processing with a computer said data to determine correlation coefficients between data parameters;
    processing said data to identify any linear dependencies between data parameters;
    processing said data to standardize the scales of said data;
    evaluating said data over a plurality of proliferation time periods and neuron numbers;
    calculating MSEs and R2's from said evaluations;
    determining an optimal proliferation time period and optimal neuron number using said calculations;
    determining whether any of the said data fall within a predetermined range; and, in the event they all are not,
    estimating a valid likelihood that said water sample will be subject to a water quality event at one or more specific times in the future, based on subsequent, periodic data values and said proliferation time period and neuron number.

2. A method as recited in claim 1, wherein said data is obtained from a sequence of successive water samples taken from a body of water.

3. A method as recited in claim 1, further comprising activating an alarm if a predicted value exceeds a corresponding threshold value or if a specific water quality condition is predicted.

4. A method as recited in claim 1, wherein said method further comprises filtering at least some of said data.

5. A computer-readable medium comprising computer instructions which, when executed by a computer, perform a method as recited in claim 1.

6. A processor on which is stored software for carrying out a method as recited in claim 1.

7. The method according to claim 1 wherein the data comprises data values for at least physical, chemical, and biological water quality conditions.

8. The method according to claim 1 wherein the data is location specific and in time series.

9. The method according to claim 1 wherein the water quality event is the presence or the possible future presence of an algal bloom.

10. The method according to claim 9, wherein the water quality parameters comprise pH, turbidity, conductivity, temperature, dissolved oxygen, total organic carbon, phycocyanin, and chlorophyll.

11. The method according to claim 1 wherein the water quality event is the presence or the possible future presence of MIB or geosmin.

12. The method according to claim 11, wherein the water quality parameters comprise pH, turbidity, conductivity, temperature, dissolved oxygen, total organic carbon, phycocyanin, and chlorophyll.

13. The method according to claim 1 wherein the water quality event is the presence or the possible future presence of nitrification.

14. The method according to claim 13, wherein the water quality parameters comprise pH, turbidity, conductivity, temperature, dissolved oxygen, total organic carbon, ammonia, total chlorine, and nitrite.

15. The method according to claim 1 wherein the water quality event is the presence or the possible future presence of TTHM or HAA5.

16. The method according to claim 15, wherein the water quality parameters comprise pH, turbidity, conductivity, temperature, dissolved oxygen, total organic carbon, ammonia, free chlorine, and DBP.

17. A method of evaluating a water sample for the possible future presence of MIB or geosmin, comprising:
    obtaining data values of pH of a water sample from a pH sensor over a period of time;
    obtaining data values of turbidity of said water sample from a turbidity sensor over a period of time;
    obtaining data values of conductivity of said water sample from a conductivity sensor over a period of time;
    obtaining data values of temperature of said water sample from a temperature sensor over a period of time;
    obtaining data values of dissolved oxygen of said water sample from a dissolved oxygen sensor over a period of time;
    obtaining data values of total organic carbon of said water sample from a total organic carbon sensor over a period of time;
    obtaining data values of phycocyanin of said water sample from a phycocyanin sensor over a period of time;
    obtaining data values of chlorophyll of said water sample from a chlorophyll sensor over a period of time;
    processing with a computer said data values of pH, said data values of turbidity, said data values of conductivity, said data values of temperature, said data values of dissolved oxygen, said data values of total organic carbon, said data values of phycocyanin, said data values of chlorophyll to determine correlation coefficients between data parameters;

processing said data values of pH, said data values of turbidity, said data values of conductivity, said data values of temperature, said data values of dissolved oxygen, said data values of total organic carbon, said data values of phycocyanin, said data values of chlorophyll to identify any linear dependencies between data parameters;

processing said data values of pH, said data values of turbidity, said data values of conductivity, said data values of temperature, said data values of dissolved oxygen, said data values of total organic carbon, said data values of phycocyanin, said data values of chlorophyll to standardize the scales of said data values of pH, said data values of turbidity, said data values of conductivity, said data values of temperature, said data values of dissolved oxygen, said data values of total organic carbon, said data values of phycocyanin, said data values of chlorophyll;

evaluating said data values of pH, said data values of turbidity, said data values of conductivity, said data values of temperature, said data values of dissolved oxygen, said data values of total organic carbon, said data values of phycocyanin, said data values of chlorophyll over a plurality of proliferation time periods and neuron numbers;

calculating MSEs and R2's from said evaluations;

determining an optimal proliferation time period and optimal neuron number using said calculations;

determining whether any of the said data values of pH, said data values of turbidity, said data values of conductivity, said data values of temperature, said data values of dissolved oxygen, said data values of total organic carbon, said data values of phycocyanin, said data values of chlorophyll are abnormal; and, in the event they all are not, estimating a valid likelihood that said water sample will be subject to MIB or geosmin at one or more specific times in the future, based on subsequent, periodic data values and said proliferation time period and neuron number.

18. A computer-readable medium comprising computer instructions which, when executed by a computer, perform a method as recited in claim 17.

19. A processor on which is stored software for carrying out a method as recited in claim 17.

20. A method of evaluating a water sample for the presence or possible future presence of nitrification, comprising:

obtaining data values of pH of a water sample from a pH sensor over a period of time;

obtaining data values of turbidity of said water sample from a turbidity sensor over a period of time;

obtaining data values of conductivity of said water sample from a conductivity sensor over a period of time;

obtaining data values of temperature of said water sample from a temperature sensor over a period of time;

obtaining data values of dissolved oxygen of said water sample from a dissolved oxygen sensor over a period of time;

obtaining data values of total organic carbon of said water sample from a total organic carbon sensor over a period of time;

obtaining data values of ammonia of said water sample from an ammonia sensor over a period of time;

obtaining data values of total chlorine of said water sample from a chlorine sensor over a period of time;

obtaining data values of nitrite of said water sample from a nitrite sensor over a period of time;

processing with a computer said data values of pH, said data values of turbidity, said data values of conductivity, said data values of temperature, said data values of dissolved oxygen, said data values of total organic carbon, said data values of ammonia, said data values of total chlorine, said data values of nitrite to determine correlation coefficients between data parameters;

processing said data values of pH, said data values of turbidity, said data values of conductivity, said data values of temperature, said data values of dissolved oxygen, said data values of total organic carbon, said data values of ammonia, said data values of total chlorine, said data values of nitrite to identify any linear dependencies between data parameters;

processing said data values of pH, said data values of turbidity, said data values of conductivity, said data values of temperature, said data values of dissolved oxygen, said data values of total organic carbon, said data values of ammonia, said data values of total chlorine, said data values of nitrite to standardize the scales of said data values of pH, said data values of turbidity, said data values of conductivity, said data values of temperature, said data values of dissolved oxygen, said data values of total organic carbon, said data values of ammonia, said data values of total chlorine, said data values of nitrite;

evaluating said data values of pH, said data values of turbidity, said data values of conductivity, said data values of temperature, said data values of dissolved oxygen, said data values of total organic carbon, said data values of ammonia, said data values of total chlorine, said data values of nitrite over a plurality of proliferation time periods and neuron numbers;

calculating MSEs and R2's from said evaluations;

determining an optimal proliferation time period and optimal neuron number using said calculations;

determining whether any of the said data values of pH, said data values of turbidity, said data values of conductivity, said data values of temperature, said data values of dissolved oxygen, said data values of total organic carbon, said data values of ammonia, said data values of total chlorine, said data values of nitrite are abnormal; and, in the event they all are not, estimating a valid likelihood that said water sample is subject to or will be subject to nitrification at one or more specific times in the future, based on subsequent, periodic data values and said proliferation time period and neuron number.

21. A computer-readable medium comprising computer instructions which, when executed by a computer, perform a method as recited in claim 20.

22. A processor on which is stored software for carrying out a method as recited in claim 20.

23. A method of evaluating a water sample for the possible future presence of TTHM or HAA5, comprising:

obtaining data values of pH of a water sample from a pH sensor over a period of time;

obtaining data values of turbidity of said water sample from a turbidity sensor over a period of time;

obtaining data values of conductivity of said water sample from a conductivity sensor over a period of time;

obtaining data values of temperature of said water sample from a temperature sensor over a period of time;

obtaining data values of dissolved oxygen of said water sample from a dissolved oxygen sensor over a period of time;

obtaining data values of total organic carbon of said water sample from a total organic carbon sensor over a period of time;

obtaining data values of ammonia of said water sample from an ammonia sensor over a period of time;

obtaining data values of free chlorine of said water sample from a chlorine sensor over a period of time;

obtaining data values of DBP of said water sample from a DBP sensor over a period of time;

processing with a computer said data values of pH, said data values of turbidity, said data values of conductivity, said data values of temperature, said data values of dissolved oxygen, said data values of total organic carbon, said data values of ammonia, said data values of free chlorine, said data values of any DBP to determine correlation coefficients between data parameters;

processing said data values of pH, said data values of turbidity, said data values of conductivity, said data values of temperature, said data values of dissolved oxygen, said data values of total organic carbon, said data values of ammonia, said data values of free chlorine, said data values of any DBP to identify any linear dependencies between data parameters;

processing said data values of pH, said data values of turbidity, said data values of conductivity, said data values of temperature, said data values of dissolved oxygen, said data values of total organic carbon, said data values of ammonia, said data values of free chlorine, said data values of any DBP to standardize the scales of said data values of pH, said data values of turbidity, said data values of conductivity, said data values of temperature, said data values of dissolved oxygen, said data values of total organic carbon, said data values of ammonia, said data values of free chlorine, said data values of any DBP;

evaluating said data of pH, said data values of turbidity, said data values of conductivity, said data values of temperature, said data values of dissolved oxygen, said data values of total organic carbon, said data values of ammonia, said data values of free chlorine, said data values of any DBP values over a plurality of proliferation time periods and neuron numbers;

calculating MSEs and R2's from said evaluations;

determining an optimal proliferation time period and optimal neuron number using said calculations;

determining whether any of the said data values of pH, said data values of turbidity, said data values of conductivity, said data values of temperature, said data values of dissolved oxygen, said data values of total organic carbon, said data values of ammonia, said data values of free chlorine, said data values of any DBP are abnormal; and, in the event they all are not, estimating a valid likelihood that said water sample will be subject to TTHM or HAA5 at one or more specific times in the future, based on subsequent, periodic data values and said proliferation time period and neuron number.

24. A computer-readable medium comprising computer instructions which, when executed by a computer, perform a method as recited in claim 23.

25. A processor on which is stored software for carrying out a method as recited in claim 23.

* * * * *